US 6,413,237 B1

(12) United States Patent
Caizza et al.

(10) Patent No.: US 6,413,237 B1
(45) Date of Patent: Jul. 2, 2002

(54) HYPODERMIC SYRINGE WITH SELECTIVELY RETRACTABLE NEEDLE

(75) Inventors: Richard Caizza, Barry Lakes; Simon Cohn, North Arlington; Jonathan Gabel, Randolph, all of NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 30 days.

(21) Appl. No.: 09/652,374

(22) Filed: Aug. 31, 2000

(51) Int. Cl.[7] ................................................. A61M 5/00
(52) U.S. Cl. ....................................... 604/110; 604/195
(58) Field of Search ................................. 604/110, 195, 604/192, 218, 263, 187, 228; 128/919

(56) References Cited

U.S. PATENT DOCUMENTS

| | | |
|---|---|---|
| 4,233,975 A | 11/1980 | Yerman |
| 4,838,863 A | 6/1989 | Allard et al. |
| 4,838,869 A | 6/1989 | Allard |
| 4,900,307 A | 2/1990 | Kulli |
| 4,927,414 A | 5/1990 | Kulli |
| 4,929,237 A | 5/1990 | Medway |
| 4,946,446 A | 8/1990 | Vadher |
| 4,955,870 A | 9/1990 | Ridderheim et al. |
| 4,966,593 A | 10/1990 | Lennox |
| 4,973,316 A | 11/1990 | Dysarz |
| 4,994,034 A | 2/1991 | Botich et al. |
| 5,011,476 A | 4/1991 | Foster |
| 5,013,301 A | 5/1991 | Marotta, Jr. et al. |
| 5,019,044 A | 5/1991 | Tsao |
| 5,045,063 A | 9/1991 | Spielberg |
| 5,046,508 A | 9/1991 | Weissler |
| 5,047,017 A | 9/1991 | Koska |
| 5,049,133 A | 9/1991 | Villen Pascual |
| 5,053,010 A | 10/1991 | McGary et al. |
| 5,064,419 A | 11/1991 | Gaarde |
| 5,084,018 A | 1/1992 | Tsao |
| 5,084,029 A | 1/1992 | Nacci nee Tagliaferri et al. |
| 5,085,640 A | 2/1992 | Gibbs |
| 5,092,853 A | 3/1992 | Couvertier, II |
| 5,114,410 A | 5/1992 | Caralt Batlle |
| 5,180,369 A | 1/1993 | Dysarz |
| 5,180,370 A | 1/1993 | Gillespie |
| 5,188,599 A | 2/1993 | Botich et al. |
| 5,201,710 A | 4/1993 | Caselli |

(List continued on next page.)

FOREIGN PATENT DOCUMENTS

EP          1 092 443 A2     4/2001

Primary Examiner—Anhtuan T. Nguyen
(74) Attorney, Agent, or Firm—Arthur D. Dawson (57) ABSTRACT

A hypodermic syringe with a selectively retractable needle includes an elongate barrel having an open proximal end, an open distal end and a hollow bore. The syringe includes an elongate plunger including a hollow outer housing having an open proximal end and an open distal end. The plunger has a hollow inner sleeve defining a cavity therein. The plunger has releasable engagement elements preventing relative axial movement between the outer housing and the inner sleeve, the elements allowing the relative axial movement when released and a distal stopper. There is an open cutter mounted at a proximal end of the inner sleeve to cut through the stopper to expose the cavity in the inner sleeve when the engagement elements are released and sufficient distal axial force is applied to the plunger. The syringe has a hub housing with an open proximal end having an inwardly projecting shoulder, a hub with a proximal flange and an axial stem, sized to fit within the hub housing. There is a spring disposed about the stem between the flange and the shoulder. The syringe has a needle with a sharp point extending outwardly. The needle retracts into the cavity in the plunger when sufficient distal force is applied to the plunger to release the engagement elements. The release allows movement of the inner sleeve with respect to the outer housing so that the cutter cuts through the stopper and the flange and the spring urges movement of the needle into the cavity.

16 Claims, 12 Drawing Sheets

U.S. PATENT DOCUMENTS

| | | |
|---|---|---|
| 5,211,629 A | 5/1993 | Pressly et al. |
| 5,232,447 A | 8/1993 | Schwarz et al. |
| 5,232,456 A | 8/1993 | Gonzalez |
| 5,267,961 A | 12/1993 | Shaw |
| 5,267,976 A | 12/1993 | Guerineau et al. .......... 604/198 |
| 5,342,308 A | 8/1994 | Boschetti .................... 604/110 |
| 5,376,080 A | 12/1994 | Petrussa ..................... 604/198 |
| 5,385,551 A | 1/1995 | Shaw ......................... 604/110 |
| 5,389,076 A | 2/1995 | Shaw ......................... 604/110 |
| 5,395,337 A | 3/1995 | Clemens et al. ............ 604/110 |
| 5,407,431 A | 4/1995 | Botich et al. ............... 604/110 |
| 5,407,436 A | 4/1995 | Toft et al. ................... 604/195 |
| 5,423,758 A | 6/1995 | Shaw ......................... 604/110 |
| 5,487,732 A | 1/1996 | Jeffrey ....................... 604/110 |
| 5,531,694 A | 7/1996 | Clemens et al. ............ 604/110 |
| 5,542,927 A | 8/1996 | Thorne et al. .............. 604/110 |
| 5,562,629 A | 10/1996 | Haughton et al. .......... 604/158 |
| 5,573,510 A | 11/1996 | Isaacson .................... 604/158 |
| 5,575,777 A | 11/1996 | Cover et al. ................ 604/198 |
| 5,578,011 A | 11/1996 | Shaw ......................... 604/110 |
| 5,605,544 A | 2/1997 | Tsao ........................... 604/110 |
| 5,613,952 A | 3/1997 | Pressly, Sr. et al. ........ 604/110 |
| 5,632,733 A | 5/1997 | Shaw ......................... 604/195 |
| 5,634,909 A | 6/1997 | Schmitz ..................... 604/196 |
| 5,637,092 A | 6/1997 | Shaw ......................... 604/110 |
| 5,643,211 A | 7/1997 | Sadowski et al. ........... 604/110 |
| 5,681,292 A | 10/1997 | Tober et al. ................ 604/195 |
| 5,685,863 A | 11/1997 | Botich et al. ............... 604/198 |
| 5,769,822 A | 6/1998 | McGary et al. ............. 604/110 |
| 5,782,804 A | 7/1998 | McMahon .................. 604/110 |
| 5,788,677 A | 8/1998 | Boitch et al. ............... 604/195 |
| 5,792,107 A | 8/1998 | Petrocelli .................... 604/110 |
| 5,800,395 A | 9/1998 | Botich et al. ............... 604/110 |
| 5,800,403 A | 9/1998 | Pressly, Sr. et al. ........ 604/195 |
| 5,853,390 A | 12/1998 | Freschi ....................... 604/110 |
| 5,882,342 A | 3/1999 | Cooper et al. .............. 604/195 |
| 5,885,257 A | 3/1999 | Badger ....................... 604/195 |
| 5,935,104 A | 8/1999 | Janek et al. ................. 604/110 |
| 5,984,898 A | 11/1999 | Garvin ....................... 604/195 |
| 6,004,278 A | 12/1999 | Botich et al. ............... 600/576 |
| 6,086,568 A | 7/2000 | Caizza |

HYPODERMIC SYRINGE WITH SELECTIVELY RETRACTABLE NEEDLE

FIELD OF INVENTION

The present invention is generally related to hypodermic syringes and more particularly to syringes that include a needle that is retractable after the intended use to substantially prevent inadvertent exposure to the needle and reuse of the syringe.

BACKGROUND

Hypodermic syringes are widely used in the medical arts for administering medicaments and for drawing body fluid samples. Generally, hypodermic syringes have a metal needle attached either fixedly or removably that has a sharpened distal point for penetrating vial stoppers or patient's skin. Hypodermic syringes and needles have been used for many years with few problems reported, when the vast numbers and needles being used are considered. More recently, with the recognition of viral diseases that are transmitted by body fluids and greater sensitivity of the need to protect health care workers from inadvertent contact with previously used needles (commonly referred to as "sharps") as well as the need to reduce criminal misuse of improperly disposed of needles and syringes, syringes and needles that include provisions to prevent reuse have been developed.

Provisions intended to prevent reuse of needles and syringes include a variety of sharps collector systems that are widely used in health care facilities. Other developments include needle attachments that may be readily broken off by practitioners once the syringe has completed its intended use. A variety of shielding mechanisms has been developed; some of which are currently commercially available. While many of these developments have reduced the incidence of inadvertent exposure of healthcare workers to sharps, most of these devices can readily be overcome by an individual determined to obtain and misuse a hypodermic syringe and needle. As a result of this problem, further developments in the art of hypodermic syringes have resulted in syringes with needles that withdraw into the body of the syringe once their intended use is completed.

U.S. Pat. No. 4,838,869 discloses a retractable hypodermic needle configured for one time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction. A potential problem with the design disclosed in this patent is that many times a practitioner may draw and expel a fluid several times during preparation for administration of a medicament, with this design, the practitioner could inadvertently discharge the retraction mechanism. Further, the design would be very difficult to manufacture in large volumes.

U.S. Pat. No. 4,900,307 discloses a hypodermic needle with an enlarged hub that provides provisions for selectively withdrawing the needle into the hub once the syringe and needle have completed their intended usage. While this disclosed design does substantially eliminate the problem of premature discharge of the retraction mechanism, the enlarged hub has a considerable "dead volume" that would result in a significant undeliverable retention of the medicament. Additionally, although the needle is secured in the hub after discharge, the syringe itself is still fully functional after the hub with the needle inside is removed.

U.S. Pat. No. 4,994,034 discloses a hypodermic injection system with a retractable needle wherein the needle retracts within the interior cavity of a syringe plunger. The disclosed invention includes a cylindrical spring housing with resilient fingers which capture a coiled spring that biasly holds a needle holder against the retaining force of the resilient fingers. The plunger in this disclosure has a frangible end, which when engaging the resilient fingers under a predetermined amount of force, dissociate which remaining inwardly-tapered shoulders spread the resilient fingers, allowing the coiled spring to eject the needle and its holder into the interior cavity of the syringe plunger. A syringe manufactured using this disclosure would be complex and difficult to assemble. It is believed that no successful commercial product has been produced using this disclosure.

U.S. Pat. No. 5,019,044 discloses a safety hypodermic syringe with a hypodermic needle fixed connected to a holder plate and constantly supported by a spring for making axial movement. The holder plate is normally retained by a clamp at a ready position for injection. When the plunger of the syringe is pushed to the bottom of the barrel, the needle is released from the clamp and is pushed by the spring to drop and further follow a rubber plug to be squeezed into a chamber in the plunger. Again, no successful commercial product has resulted from this disclosure, which would be complex to manufacture and appears to have a considerable undeliverable dead volume.

Another example of a syringe with a retractable needle is disclosed in U.S. Pat. No. 5,053,010. The disclosed syringe retracts the needle into a hollow plunger additional pressure on the plunger after the contents of the syringe are expelled. The disclosed design incorporates a sliding elastomeric seal which displaces from its forward position to a retracted position, thereby allowing additional forward travel of the plunger to actuate the retraction mechanism. A problem reported with this design is that, because of the soft nature of the seal, the seal may be prematurely displaced during its use in an injection. Attempts to overcome this difficulty by increasing the stiffness of the sealing member could impair the seal integrity.

U.S. Pat. No. 5,180,369 discloses a self destructive syringe assembly having a needle cannula fixed to a slidable piston. The slidable piston and slidable piston flange are held within the barrel of the syringe assembly by a compressed spring, a guide tube and a shatter ring. The plunger of the syringe assembly is a hollow elongated tube with a thumb flat at one end, a sliding gasket, a plunger shatter plate and a hook rim at the other end. The patent reports that when medicament is injected, the elongated hollow plunger is further thrust into the shatter ring, the shatter ring shatters, further allowing the slidable piston and slidable piston flange to thrust into the plunger shatter plate to shatter. The shattering of the plunger shatter plate causes the slidable piston and needle cannula to be thrust into the hollow plunger by the spring and is thus prevented from re-entering the guide tube. Again, no successful commercial product has resulted from this disclosure.

U.S. Pat. No. 5,180,370 discloses a syringe which has an internal mechanism for retracting the needle into the syringe after the injection has been given. In one disclosed embodiment, the needle is manually retracted by pulling back on the plunger, and in another, the needle is propelled by a compressed spring into a hollow chamber within the plunger. A syringe produced with this disclosure would be complex to manufacture, and no successful commercial product has resulted from this disclosure.

U.S. Pat. 5,188,599 discloses a hypodermic injection system with a needle that retracts within an interior cavity of the syringe plunger. The needle when retracted is held within the plunger. The disclosed device includes a cylindrical spring housing that has resilient fingers which capture a spring under bias holding a needle holder against the retaining force of resilient fingers. The plunger has a frangible end, which dissociates when the outwardly tapered shoulders spread the resilient fingers, allowing the coiled spring to eject the needle and its holder into the interior cavity of the syringe plunger. The patent also discloses a body fluid sampling device that includes a double-ended needle for communication with an evacuated blood collection tube. This patent also includes a review of several earlier disclosures related to retractable needles. Attempts have been made to produce commercial products based on the disclosures of this patent, but as yet there is no successful commercial product.

U.S. Pat. No. 5,201,710 discloses a syringe fitted with a clamping device for the needle and with a mechanism to enable the needle to be automatically retractable into the syringe body at the end of an injection. The disclosed device includes inner and outer cylinders, openings at the ends of the outer cylinder, a third opening at an end of the inner cylinder and a closure for the third opening. The disclosed device further includes a needle with a head, a seal, a first spring to push the needle against the closure and a clamping device loaded by a second spring to maintain outward to the syringe and to release the needle. There is a diaphragm in the closure that bends before breaking and a sharp element to break the diaphragm. There also is a closure to prevent the needle from being accessible and a stop to prevent the second cylinder from being moved outwardly after the syringe is used. As is apparent from the description, the device disclosed by this patent is complex and would be difficult to assemble. No successful commercial product has resulted from the disclosure in this patent.

U.S. Pat. No. 5,385,551 discloses a non-reusable medical device that has a needle which is retractable by depression a plunger slidably mounted in the device. The disclosed device includes a front-mounted retraction mechanism that has a needle holder connected to the needle. The needle holder is supported along the axis of the device by a frictionally engaged retainer ring member coupled to the needle holder along an axially aligned sliding interface. The needle holder and retainer are positioned in the front portion of a hollow body. The front of a movable member or plunger presses against the retainer member passing around the needle holder which cannot move forward, thereby separating the retainer from the needle holder. The separation occurs by gradually reducing the extent of the sliding interface area until the retainer member pops loose from the needle holder whereupon the needle holder and needle are retracted into a cavity in the plunger in response to a retraction force applied to the needle holder by a previously compressed spring. Again, the device disclosed in this patent is complex, difficult to manufacture and appears to have significant undeliverable dead volume. Attempts have been made to commercialize products from this disclosure with only limited success.

U.S. Pat. No. 5,407,436 discloses a hypodermic syringe that has a hollow needle that is automatically retractable after use. The disclosed syringe includes a one-piece body molding has a main chamber for a plunger, sample container or drug cartridge, a forward chamber to house a spring to bias a needle holder, and internal latching formations to retain the needle holder with the spring compressed in the forward chamber until automatic retraction when the latching formations are released by end of plunger movement. The patent discloses that the sealing between the plunger and the body is accomplished by an over-sized plunger head that forces head and wall deformation. The disclosed spring has seals at both ends for the forward chamber. The patent teaches that the needle, its holder, spring and seals can be installed using a sliding guide. In using a syringe produced using this disclosure, the practitioner would need to exercise care when drawing and expelling a fluid during filling, because the retraction of the needle is activated by depressing the plunger sufficiently to engage cooperating latches. The engagement occurs at the bottom of the stroke to expel fluid from the syringe.

U.S. Pat. No. 5,769,822 discloses a non-reusable syringe with a hollow plunger that has a seal member thereon. The position of the plunger and the seal relative to the barrel permits the plunger, with sufficient strength, to carry applied pressure through the device during injection of a fluid and yet permit the seal disposed at one end of the plunger to have maximum sealing integrity between the plunger and a cylindrical barrel disposed around the exterior of the plunger to abate leakage of the liquid in a chamber within the barrel, as the plunger is manipulated from an expanded position to and expended position and thereafter to a third or collapsed position.

U.S. Pat. No. 6,010,486 discloses a retracting needle syringe that substantially prevents reuse of the syringe by destroying the plunger rod and the needle hub and additionally, retracts the needle into the plunger rod. The disclosed syringe includes provisions that upon fully depressing the plunger rod and applying distally directed axial force, a frangible portion of the inner hub is broken and the plunger tip dislodges to allow a spring to urge a cutter to open the chamber inside the plunger.

Most of the devices discussed in the above referenced disclosures are somewhat complex, and many require manufacture and assembly of parts with potentially difficult assembly or tight tolerance requirements. Many of the designs depend upon a careful application of forces by the practitioner to draw and expel fluids from the syringe. Also, if the tolerances between the multiple components of the device are not carefully adhered to during manufacture and assembly, normal usage may result in premature activation of the retraction function of the syringe. The problem of premature activation of the retraction function is particularly critical for syringes intended for use in "High Pressure" applications. Examples of high pressure applications include delivery of radiopaque dyes for radiological procedures, delivery of medicaments with high viscosities and the like. Current conventional syringes are considered by users to be virtually fault-free and reliable. They are used for a variety of different procedures involving both "one-shot" fill and inject procedures, as well as more complex mixing measuring and delivery functions. In order for a retractable syringe to displace these functional, utilitarian and reliable conventional syringes, the retractable syringe should not significantly interfere with the users current practices, it needs to be substantially reliable and their cost should not be prohibitive. Current conventional syringes are often manufactured at rates of several hundred per minute and their cost is generally not a significant factor in their usage. Reviewing the disclosures above, one skilled in the art of high volume manufacturing recognizes that assembling millions of most of these relatively complex devices is a daunting task. Additionally, many of the disclosed devices have substantial undeliverable "dead volumes" that confound the practitioners need for accurate delivery or that may waste a substantial percentage of a high cost medicament. The need thus exists for a selectively retractable syringe that is capable of being used in "high pressure" applications, and also is capable of being manufactured at high volumes. The syringe should be sufficiently non-complex to be reliable in use when produced at volumes of millions per year. Such a device is disclosed herein below.

SUMMARY

A hypodermic syringe with a selectively retractable needle of the present invention includes an elongate barrel having an open proximal end, an open distal end and a hollow bore therethrough. The syringe includes an elongate plunger sized to fit slidably within the barrel, the plunger comprising a hollow outer housing having an open proximal end and an open distal end. The plunger has a hollow inner sleeve having a sidewall defining a cavity therein with open proximal and distal ends. The inner sleeve is disposed within and sized to fit slidably within the hollow outer housing. The plunger has releasable engagement elements preventing relative axial movement between the outer housing and the inner sleeve, the elements allowing the relative axial movement when released. The plunger further includes a stopper mounted at the distal end of the outer housing for occluding the open distal end that forms a slidable seal with the hollow bore of the barrel to define a chamber for drawing and expelling fluid. The plunger also includes an open cutter mounted at the proximal end of the inner sleeve disposed to cut through the stopper to expose the cavity in the inner sleeve when the engagement elements are released and sufficient distal axial force is applied to the plunger. The syringe has a hub housing having an open proximal end having an inwardly projecting shoulder, a passageway therethrough having an inside the said barrel. There is a hub that proximal flange, an axial stem with a distal end having a passage therethrough, sized to it within the hub housing with the stem extending distally. The flange defines a distal end of the chamber. There is an elongate spring disposed about said stem and compressed to provide a bias between the flange and the inwardly projecting shoulder of hub housing. The syringe has an elongate needle with a sharp distal point, a proximal end and a fluid path therethrough mounted in the passage in the hub with the distal point extending outwardly and the fluid path in communication with the chamber. The needle is retracted into the cavity in the plunger when sufficient distal force, greater than the force required to expel fluid from the chamber, is applied to the plunger thereby releasing the engagement elements. The release allows relative movement of the inner sleeve with respect to the plunger outer housing so that the cutter cuts through the stopper and the flange. When the flange and the stopper are cut through, the bias of the spring to urges a sufficient movement of the stem having the needle mounted therein into the cavity in the inner sleeve thereby substantially preventing inadvertent exposure of said point of said needle.

The syringe of the invention has an undeliverable "deadspace" volume substantially similar to conventional fixed needle syringes, i.e., substantially no undeliverable volume. The syringe of the invention is as suitable for use in drawing, measuring, mixing and delivering of medicaments at high pressure as conventional syringes. Unlike many of the devices disclosed above, the syringe of the invention is substantially unlikely to be inadvertently retracted by a user following currently used practices and procedures. The syringe of the invention does not depend on a user having to exercise substantially more care than with a conventional syringe when drawing and mixing fluids in the syringe to avoid inadvertent activation, and importantly, the syringe of the invention is compatible with the efficiency of high volume automated manufacture that utilizes much existing manufacturing equipment. Once needle is retracted in the syringe of the invention, the syringe cannot be restored to functionality, even by an individual determined to misuse the syringe, as the hub flange is cut through and the stopper is cut through rendering the syringe substantially unusable. Further, the needle point is protected from inadvertent contact.

DETAILED DESCRIPTION

While this invention is satisfied by embodiments in many different forms, there are shown in the drawings and herein described in detail, embodiments of the invention with the understanding that the present disclosure to be considered as exemplary of the principles of the present invention and is not intended to limit the scope of the invention to the embodiments illustrated. The scope of the invention is measured by the appended claims and the equivalents. In this disclosure, a convention is followed wherein the distal end of the device is the end closest to a patient and the proximal end of the device is the end away from the patient and closest to a practitioner.

Referring to FIGS. 1–13, a hypodermic syringe 10 with a selectively retractable needle 12 of the present invention includes an elongate barrel 14 having an open proximal end 16, an open distal end 18 and a hollow bore 20 therethrough. Syringe 10 includes an elongate plunger 22 sized to fit slidably within barrel 14. Plunger 22 including a hollow outer housing 24 having an open proximal end 26 and an open distal end 28. Plunger 22 has a hollow inner sleeve 30 having a sidewall 32 defining a cavity 34 therein with an open proximal end 36 and an open distal end 38. Inner sleeve 30 is disposed within and sized to fit slidably within hollow outer housing 24. Sidewall 32 further includes a proximal portion having at least one slot 40, preferably two slots 40, therethrough and a thumbpress 42 that is fit within inner sleeve 30 having at least one, preferably two, flexible lugs 44, sized and shaped to protrude through slot 40 in inner sleeve 30 and substantially prevent movement of inner sleeve 30 with respect to outer housing 24.

Preferably, the engagement between inner sleeve 30 and outer housing 24 of plunger 22 also includes an enlarged area 29 of distal portion 28 of inner sleeve 30 disposed to provide a detent 78 with outer housing 24. Detent 78 serves to keep inner sleeve and outer housing 24 engaged until a distal force, preferably greater than a force generated by a load between about eight to about twelve pounds, is applied to plunger 22. The function of detent 78 is to prevent lugs 44 from engaging proximal end 16 of the barrel. After detent 78 is overcome, lugs 44 engage proximal end 16 of the barrel and when a sufficient force, preferably greater than a force generated by a load of about fifteen pounds, is applied to plunger 22 are sufficiently deflected to allow movement of inner sleeve 30 with respect to outer housing 24 of the plunger.

Plunger 22 further includes a stopper 46 mounted at distal end of the outer housing for occluding the open distal end that forms a slidable seal with hollow bore 20 of barrel 14 to define a chamber 48 for drawing and expelling fluid. Plunger 22 also includes an open cutter 50 mounted at proximal end 36 of the inner sleeve disposed to cut through stopper 46 to expose cavity 34 in the inner sleeve when lugs 44 are released and sufficient distal axial force is applied to plunger 22. Syringe 10 has a hub housing 52 having an open proximal end 54 that has an inwardly projecting shoulder 56, a passageway 58 therethrough. There is a hub 60 that has a proximal flange 62, an axial stem 64 with a distal end 66 having a passage 68 therethrough, sized to fit within hub housing 52 with stem 64 extending distally. Flange 62 defines a distal end of the chamber 48. There is an elongate spring 70 disposed about stem 64 and compressed to provide a bias between flange 62 and inwardly projecting shoulder 56 of hub housing 52. Syringe 10 with elongate needle 12 has a sharp distal point 72, a proximal end 74 and a fluid path 76 therethrough. Proximal end 74 of the needle is mounted in passage 68 in hub 60 with distal point 72 extending outwardly and fluid path 76 in communication with chamber 48. Needle 12 is retracted into cavity 34 in plunger 22 when sufficient distal force, greater than the force required to expel fluid from chamber 48, is applied to plunger 22 thereby releasing the engagement elements. The release allows relative movement of inner sleeve 30 with respect to plunger outer housing 24 so that cutter 50 cuts through stopper 46 and flange 62. When flange 62 and stopper 46 are cut through, the bias of spring 70 to urges a sufficient movement of stem 64 having needle 12 mounted therein into cavity 34 in inner sleeve 30 thereby substantially preventing inadvertent exposure of point 72 of needle 12.

Figure 4:
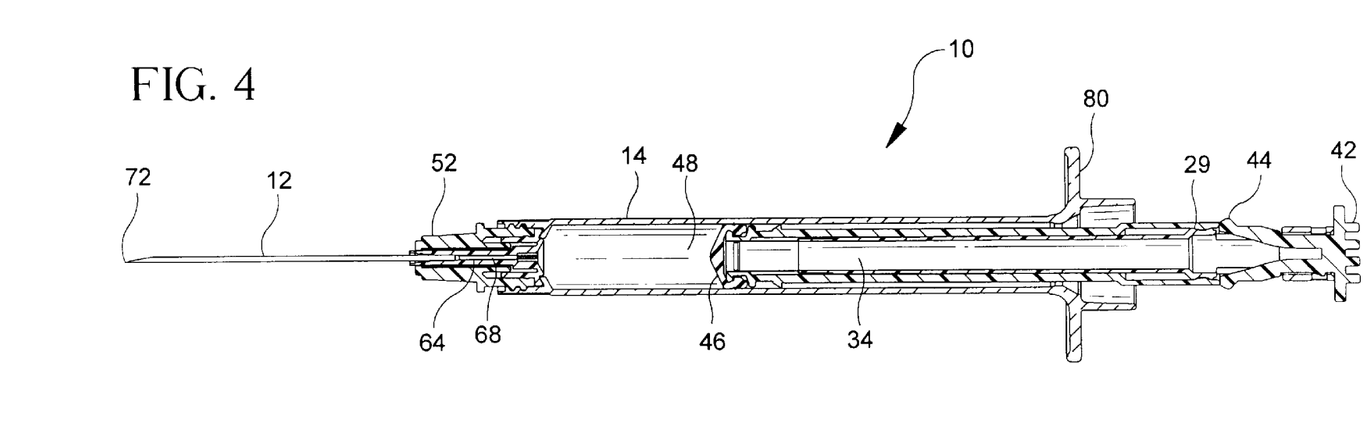
FIG. 4 is a cross-sectional view of the syringe of FIG. 1 taken on the line 4—4.
Figure 5:
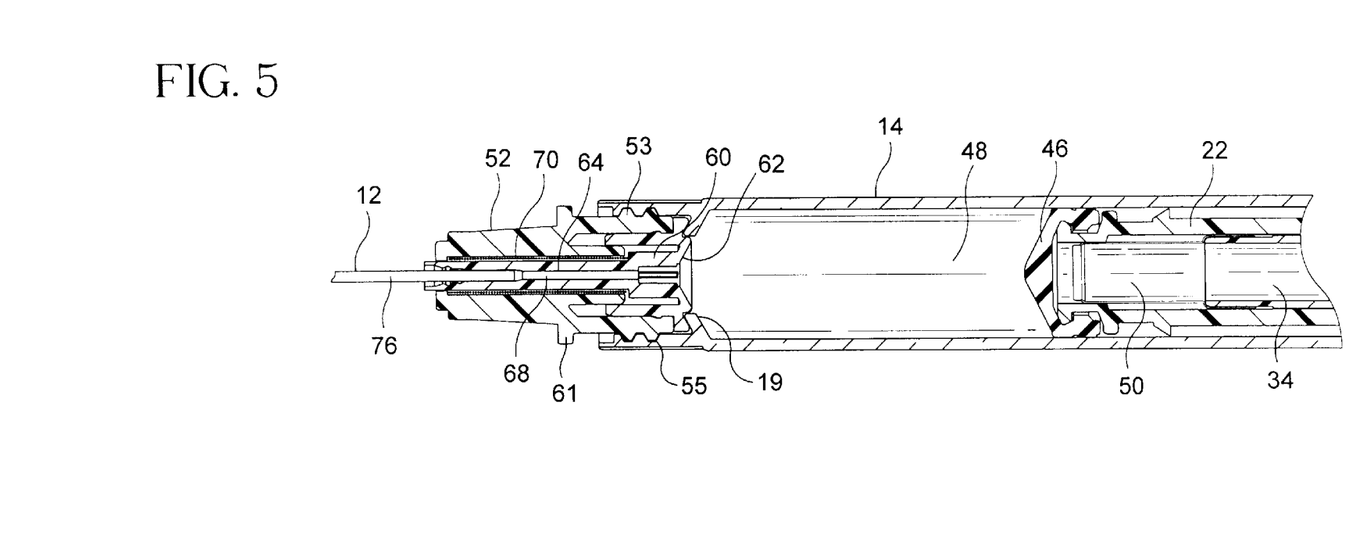
FIG. 5 is an enlarged cross-sectional view of the distal portion of the view of FIG. 4.
Figure 6:
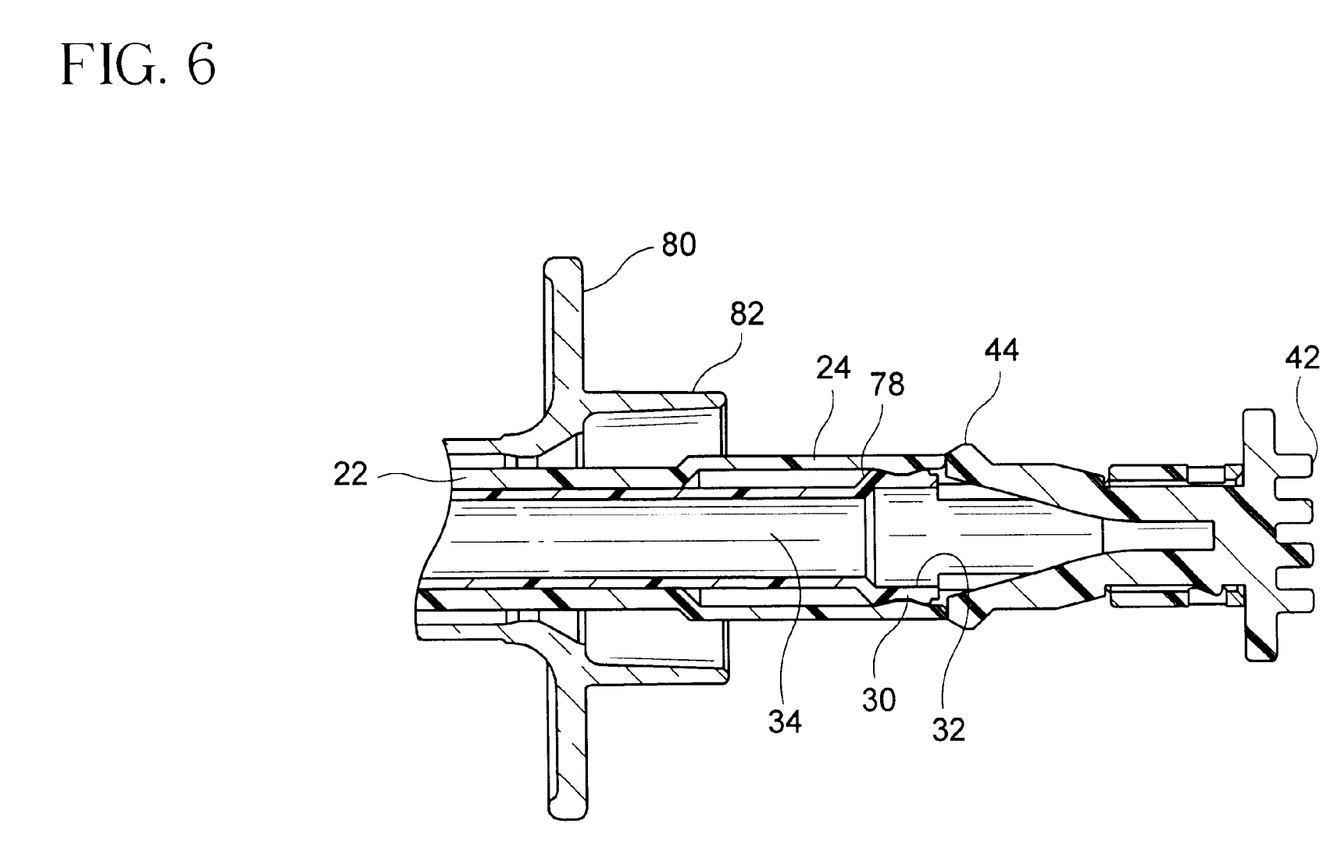
FIG. 6 is an enlarged cross-sectional view of the proximal portion of the view of FIG. 4.

As related in the background above, hypodermic syringes are often used in applications requiring "high pressure" delivery. Examples of these applications include administration of radiopaque dyes for radiological procedures and administration of high viscosity medicaments. Syringe 10 of the invention is well suited for these applications, because initiation of the needle retraction process is not dependent on balanced forces or tight tolerances for interaction of one part with another. Referring to FIGS. 4, 5 and 6, plunger 22 with outer housing 24 and inner sleeve 30 are joined together by lugs 44 and detent 78 so that proximal and distal movement of stopper 46 draws and expels fluid from chamber 48. Cutter 50, mounted on inner sleeve 30, is positioned proximally to stopper 46 and remains there until chamber 48 is emptied of fluid. Experimental use of load cell equipped syringes has determined that forces as would be exerted by a load of between about eight and twelve pounds are sufficient to expel most fluids in most applications from chamber 48.

Figure 7:
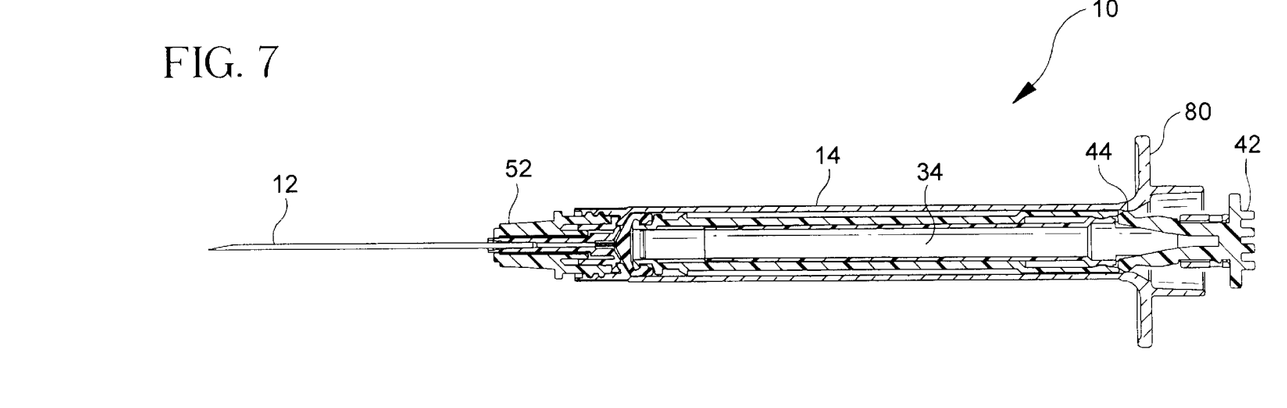
FIG. 7 is a cross-sectional view of the syringe of FIG. 1 with the plunger in the position to expel substantially all fluid from the syringe.
Figure 8:
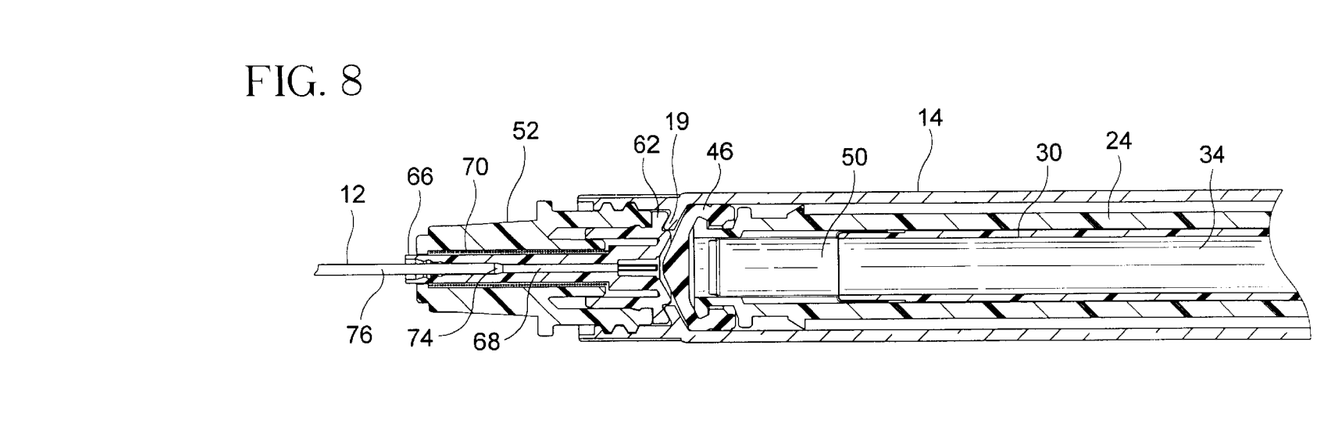
FIG. 8 is an enlarged cross-sectional view of the distal portion of the view of FIG. 7.
Figure 9:
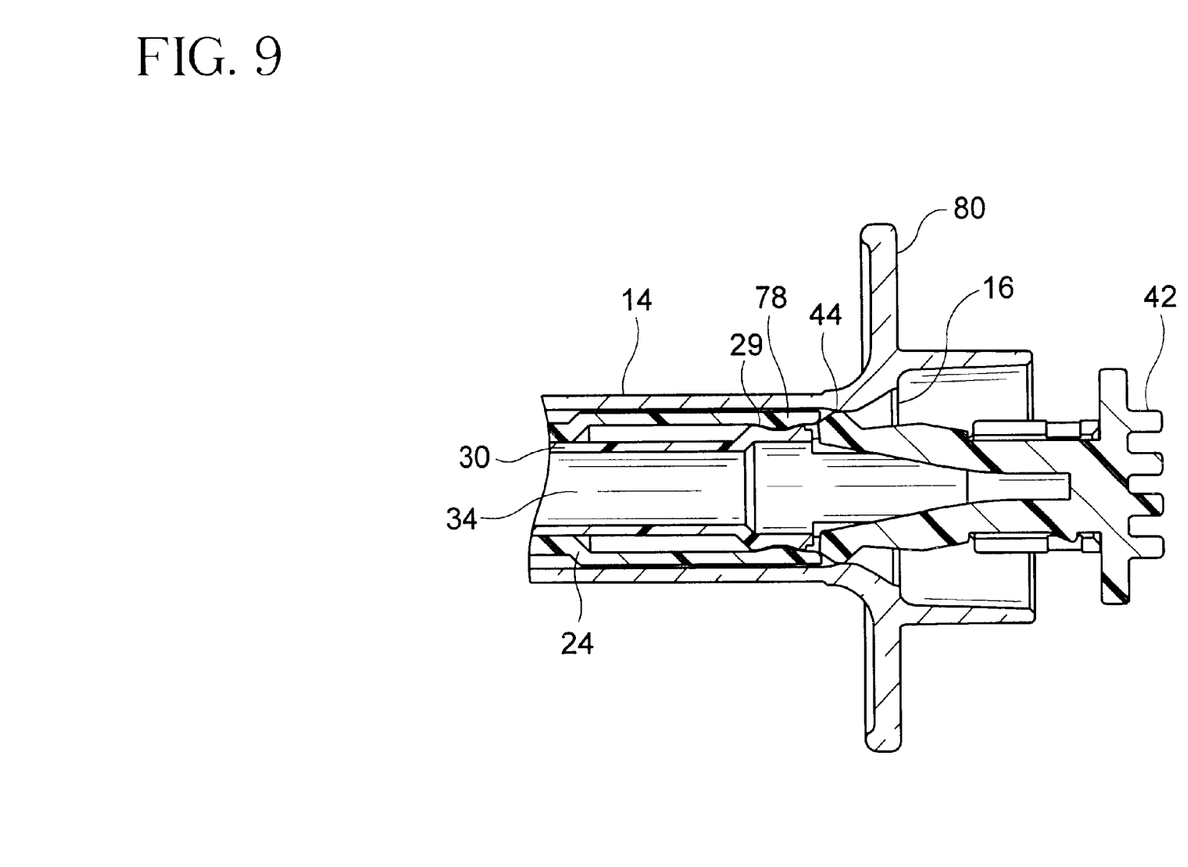
FIG. 9 is an enlarged cross-sectional view of the proximal portion of the view of FIG. 7.
Figure 10:
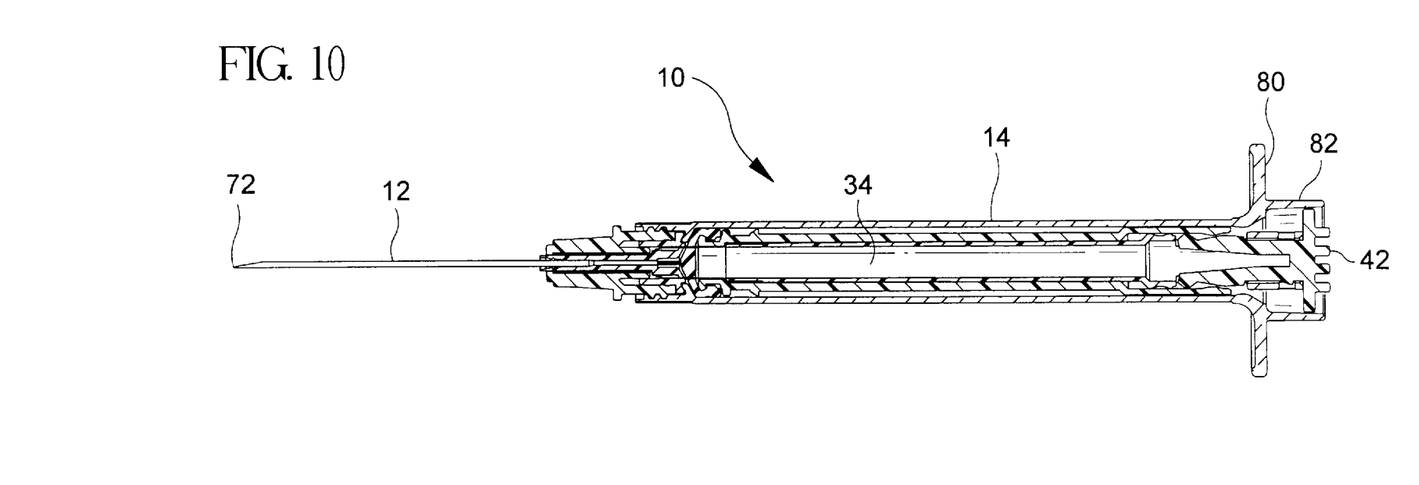
FIG. 10 is a cross-sectional view of the syringe of FIG. 1 with the plunger advanced distally beyond the position, shown in FIG. 7, to expel substantially all fluid from the syringe.
Figure 11:
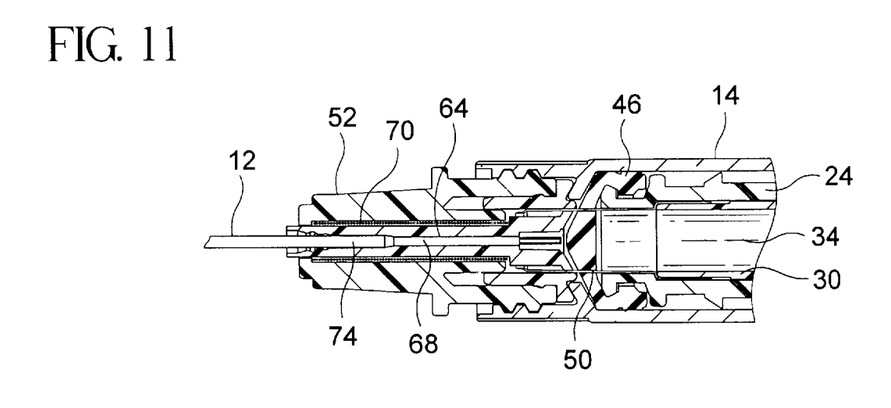
FIG. 11 is an enlarged cross-sectional view of the distal portion of the view of FIG. 10.
Figure 12:
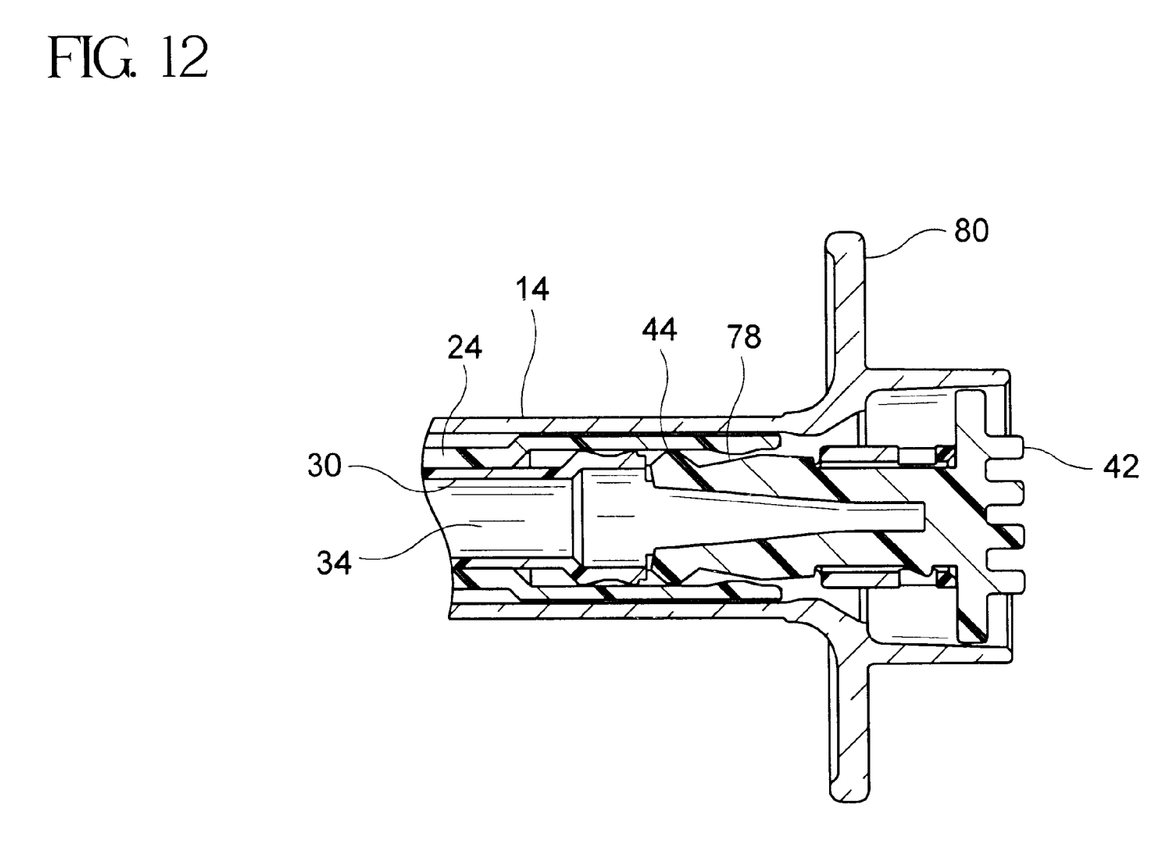
FIG. 12 is an enlarged cross-sectional view of the proximal portion of the view of FIG. 10.
Figure 13:
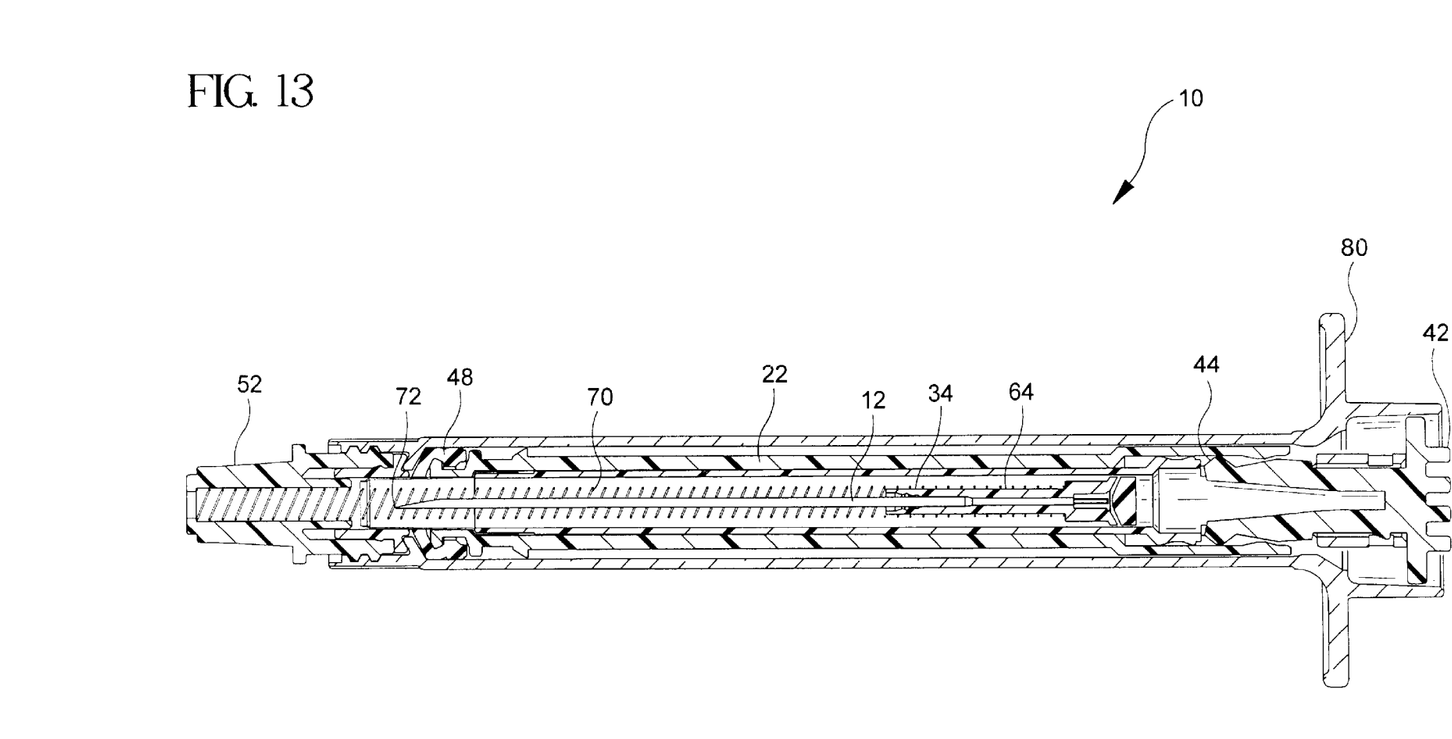
FIG. 13 is a cross-sectional view of the syringe of FIG. 1, analogous to FIG. 4, with the retraction mechanism fully activated.

Referring now to FIGS. 7, 8 and 9, as detent 78 is overcome, plunger 22 is fully distal in barrel 14 and chamber 48 is substantially empty of fluid with substantially no undeliverable volume ("no dead-space"). Lugs 44 are engaging proximal end 16 of the barrel and as a distal force that would be exerted by a load of about fifteen pounds is applied to thumbpress 42, lugs 44 are deflected inwardly by the barrel to allow relative movement of inner sleeve 30 with respect to outer housing 24 that has stopper 46 mounted at distal end 28. As illustrated in FIGS. 10, 11 and 12, cutter 50 cuts through stopper 46 to expose cavity 34 in sleeve 30. As inner sleeve 30 advances distally, cutter 50 cuts through flange 62 to release stem 64 with needle 12 mounted therein so that spring 70 urges the cut portion of stopper 46, the cut portion of flange 62 with stem 64 and needle 12 into cavity 34, as best seen in FIG. 13. With the withdrawal of needle 12 into cavity 34, syringe 10 is substantially non-functional and substantially cannot be restored to functionality. Additionally, personnel are substantially protected from inadvertent exposure to sharp distal point 72 of the needle.

Figure 14:
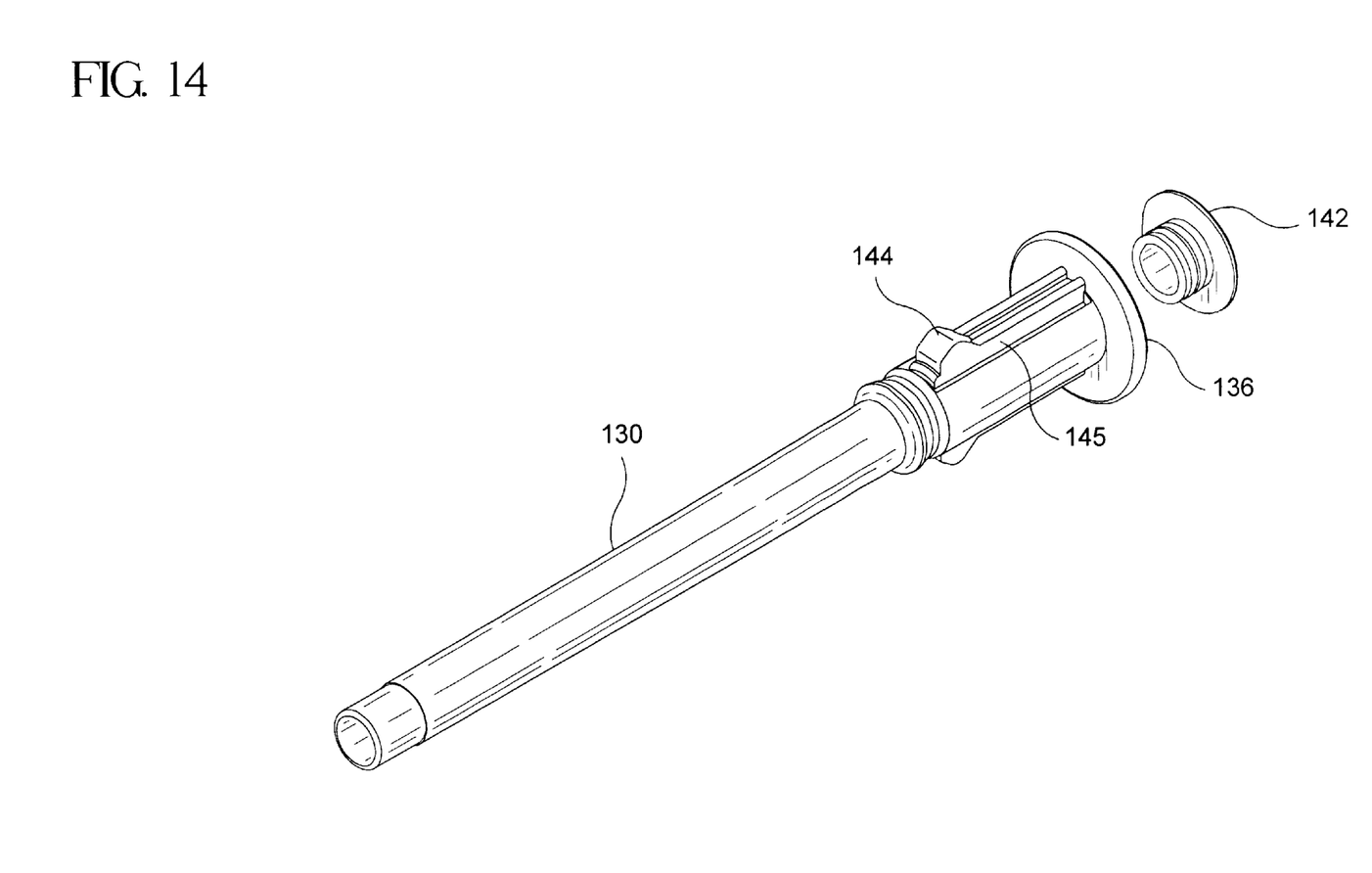
FIG. 14 is a perspective view of an alternate embodiment of a portion of the invention of FIG. 1.
Figure 15:
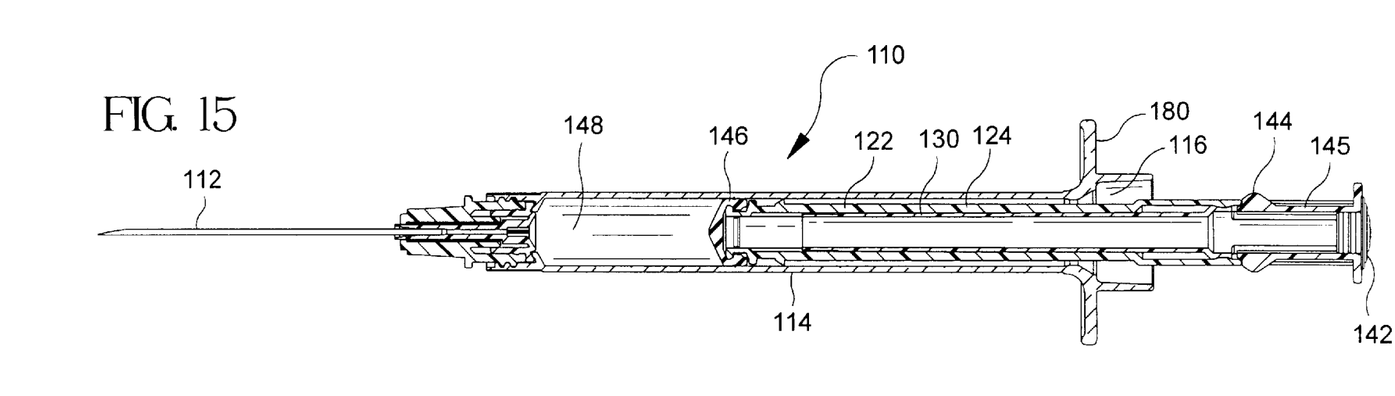
FIG. 15 is a cross-sectional view of the syringe of the invention, analogous to FIG. 4, incorporating the alternate embodiment portion illustrated in FIG. 14.
Figure 16:
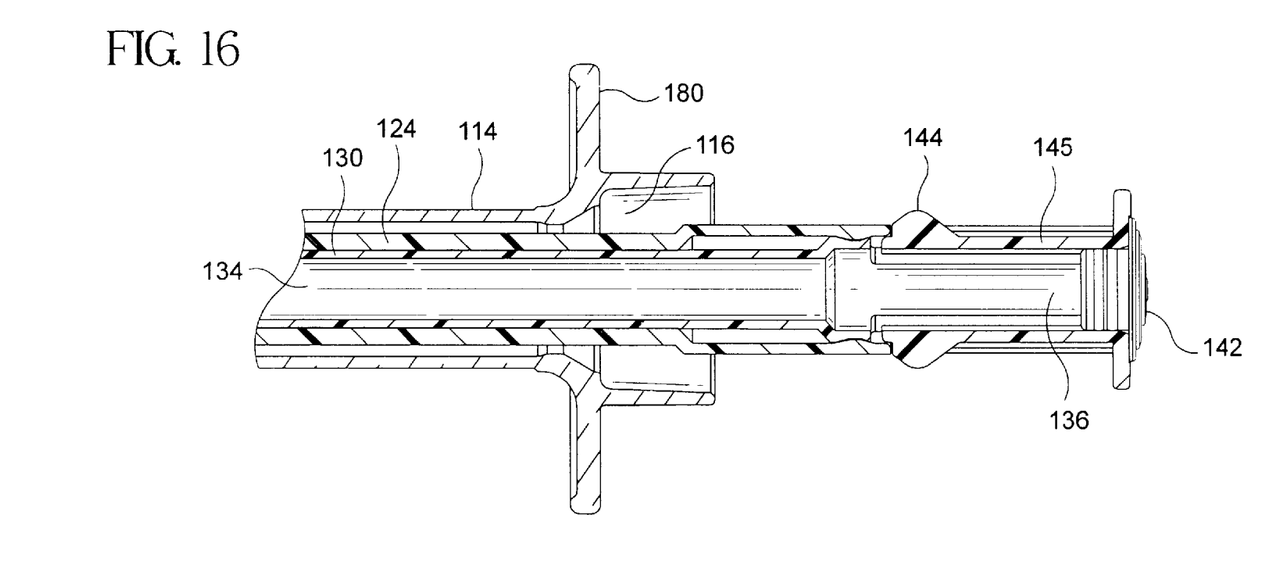
FIG. 16 is an enlarged cross-sectional view of the proximal portion of the view of FIG. 15.

Referring now to FIGS. 14, 15 and 16, an alternate embodiment to for plunger 22 is illustrated. In this embodiment, elements that are substantially the same as those of FIGS. 1–13 are assigned similar reference characters with the addition of hundreds digits. FIG. 14 illustrates inner sleeve 130 of plunger 122. In this embodiment, lugs 144 are integrally formed as cantilevers 145 with hollow inner sleeve 130. In this embodiment, thumbpress 142 is a plug that occludes open proximal end 136 of inner sleeve 130. FIGS. 15 and 16 illustrate plunger 122 in barrel 114 with chamber 148 for drawing and expelling fluid. FIG. 16 illustrates the interaction of lugs 144 with outer housing 124 substantially preventing movement of inner sleeve 130 with respect to outer housing 124 as long as lugs 144 are not in contact with proximal end 116 of barrel 114. The function of syringe 110 is similar to that described above for syringe 10 and illustrated in FIGS. 1–13.

Referring to FIGS. 1–13, preferably, hub housing 52, hub 60 with needle 12 attached are formed into an assembly 61. Housing 52 preferably includes male threads 53 that cooperate with female threads 55 located at distal end 18 of barrel 14. Threads 53 and 55 allow the releasable attachment of assembly 61 to barrel 14. While threads are preferred, other forms of attachment are known and attachment for attaching assembly 61 to barrel 14 may be preferred for particular applications such as press-fit, snap fit and the like and are considered within the scope of the invention. Preferably, barrel distal end 18 further includes an inwardly extending seal 19, best seen in FIGS. 5 and 8, to engage flange 62 of hub 60 when hub housing 52 having hub 60 disposed therein, thereby to form a substantially fluid tight seal between flange 62 and barrel 14.

Figure 1:
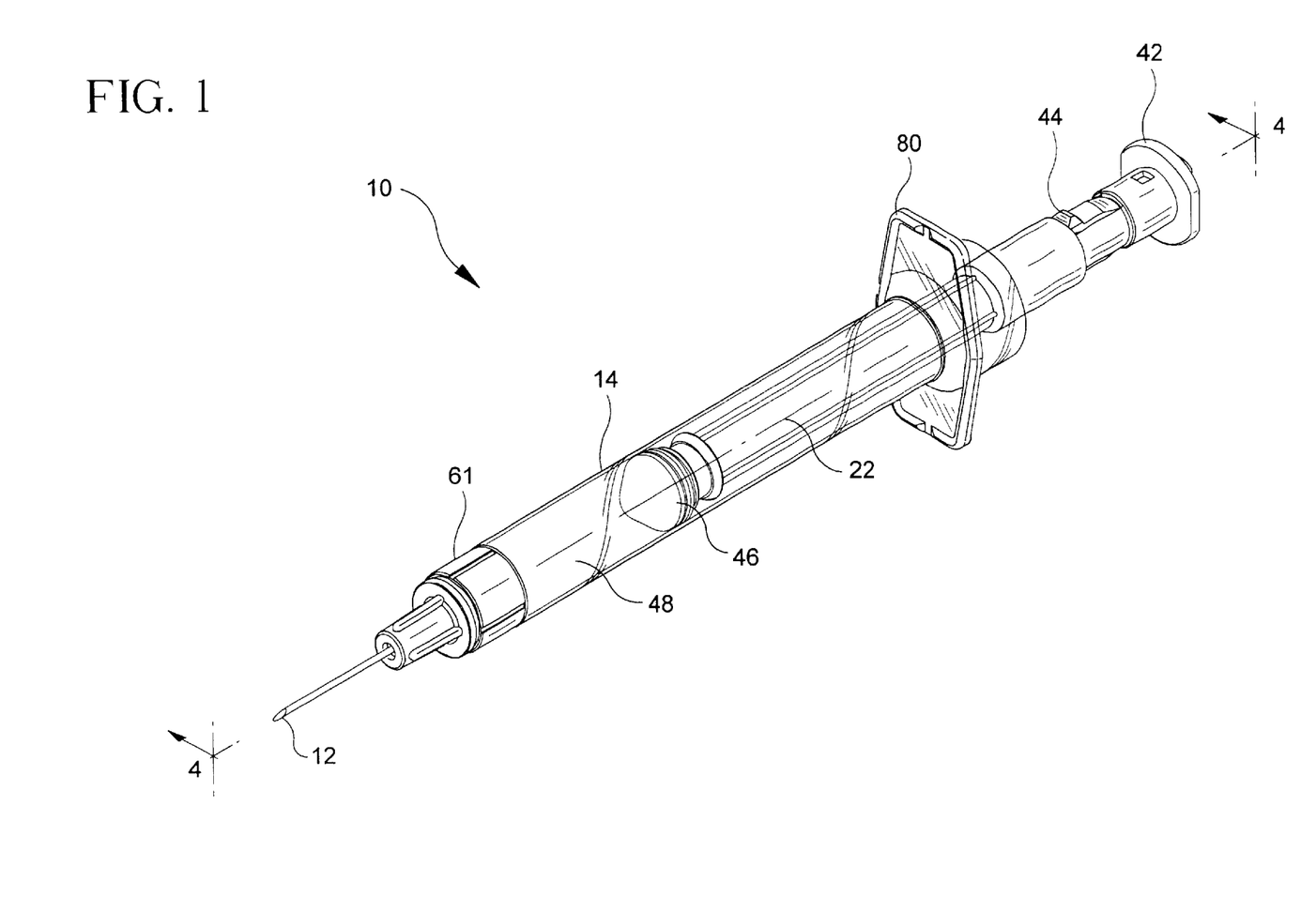
FIG. 1 is a perspective view of hypodermic syringe of the invention.
Figure 2:
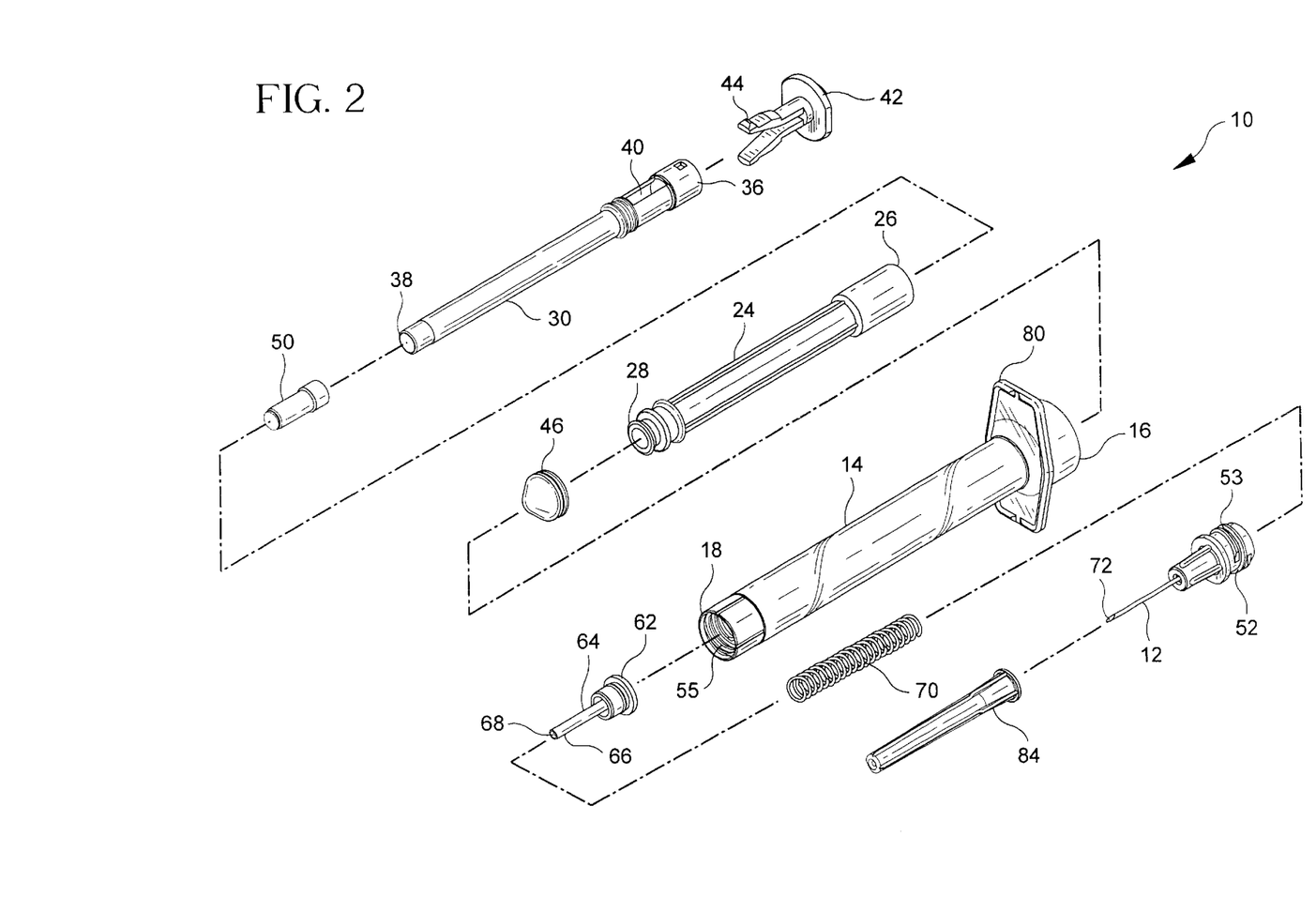
FIG. 2 is an exploded perspective view of the syringe of FIG. 1.
Figure 3:
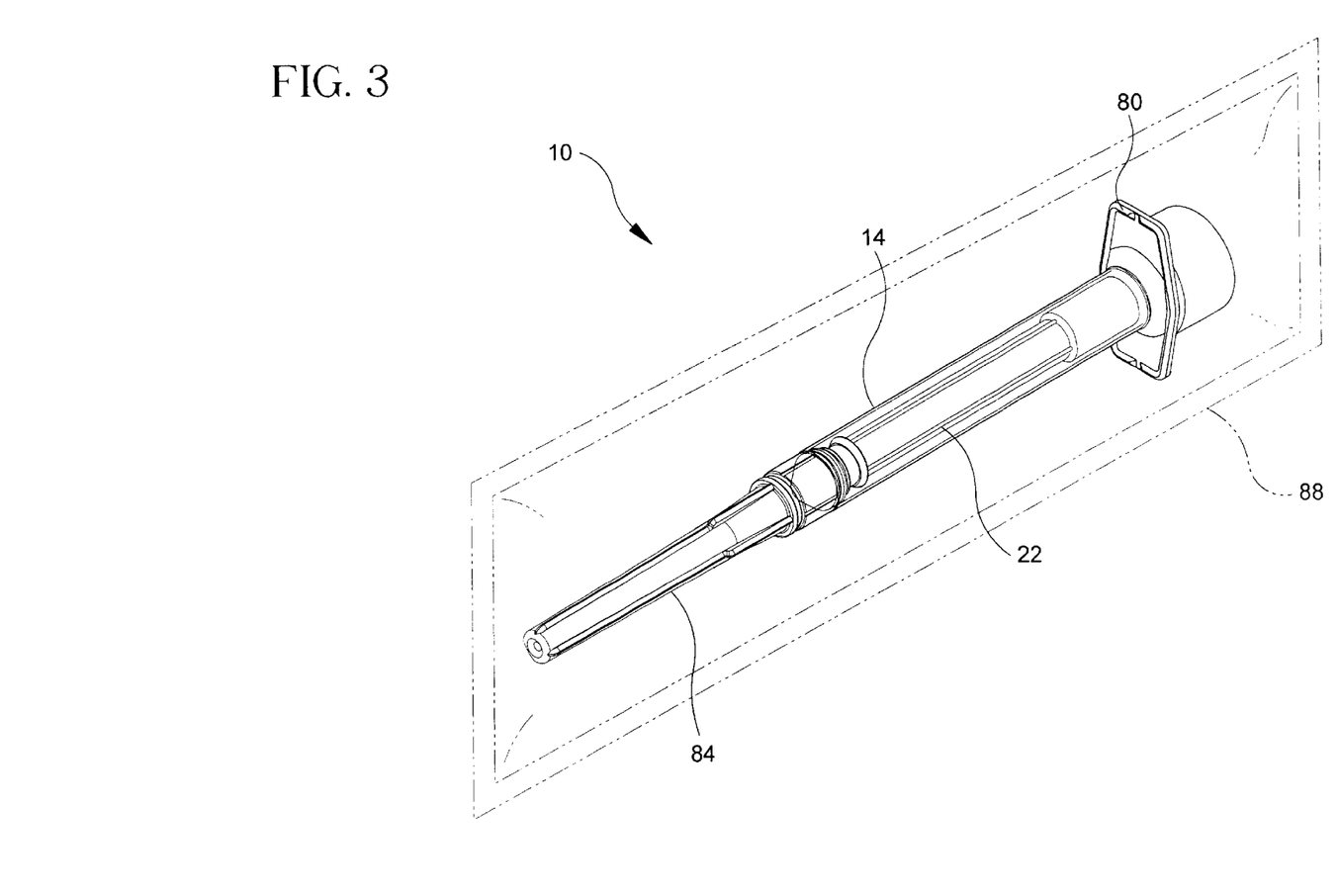
FIG. 3 is perspective view of the syringe of the invention in a package.

Referring to FIGS. 1–3, syringe 10 preferably includes a finger flange 80 at proximal end 16 of the barrel to assist a user in grasping the syringe and applying distal pressure to thumbpress 42. Syringe 10 also preferably includes a proximal collar 82 to receive thumbpress 42 when plunger 22 is fully depressed. Preferably syringe 10 is fitted with a needle shield 84 to protect sharp distal point 72 of needle 12 from damage prior to use. Syringe 10 is preferably sealed in a package 88 formed from materials substantially resistant to the passage of microorganisms and exposed to conditions that substantially render microorganisms therewithin substantially non-viable. Suitable materials for forming package 88 include, but are not limited to paper, non-wovens, polymeric film, metallic foil and combinations thereof. Suitable conditions for rendering microorganisms substantially non-viable include, but are not limited to, exposure to ionizing radiation, chemical sterilants and the like.

Barrel 14 is may be formed from thermoplastic materials such as polypropylene, polycarbonate, polyethylene and copolymers. Plunger 22 is preferably formed from polypropylene, polyethylene, polystyrene and the like. Cutter 50 is preferably formed form a metallic material such as stainless steel using a deep draw process. Cutter 50 preferably is subjected to secondary processes such as electrochemical treatment, honing, sharpening, grinding and combinations of these process to produce a sharpened surface at the distal end of cutter 50.

Syringe 10 of the invention provides practitioners having demands for high pressure delivery of drugs with a reliable device. The components of syringe 10 are compatible with the requirements for high speed manufacture because, as described above, many of the components of syringe 10 do not differ substantially in shape or balance from similar components of conventional syringes.

What is claimed is:

1. A hypodermic syringe with a selectively retractable needle comprising:
   an elongate barrel having an open proximal end, an open distal end and a hollow bore therethrough;
   an elongate plunger sized to fit slidably within said barrel, said plunger comprising a hollow outer housing having an open proximal end and an open distal end, a hollow inner sleeve having a sidewall defining a cavity therewithin, an open proximal end and an open distal end, said inner sleeve disposed within and sized to fit slidably within said hollow outer housing, and releasable engagement means for engaging said inner sleeve and said outer housing thereby preventing relative axial movement between said outer housing and said inner sleeve, said means allowing said relative axial movement when released, said plunger further including a stopper mounted at said distal end of said outer housing for occluding said open distal end and sized to form a slidable seal with said hollow bore of said barrel to define a chamber for drawing and expelling fluid, and a open cutter mounted at said proximal end of said inner sleeve and disposed to cut through said stopper to expose said cavity in said inner sleeve when said engagement means are released and sufficient distal axial force is applied to said plunger;
   a hub housing having an open proximal end having an inwardly projecting shoulder, a passageway therethrough having an inside surface, a distal end and an attachment for attaching said hub to said proximal end of said barrel;
   a hub comprising a proximal flange, an axial stem with a distal end having a passage therethrough, said hub sized to fit within said hub housing with said stem extending distally and said flange defining a distal end of said chamber;
   an elongate spring disposed about said stem and compressed to provide a bias between said flange and said inwardly projecting shoulder of hub housing;
   an elongate needle having a sharp distal point, a proximal end and a fluid path therethrough, said needle being mounted in said passage in said hub with said distal point extending outwardly and said fluid path in communication with said chamber, said needle being retracted into said cavity in said plunger when sufficient distal force, greater than the force required to expel fluid from said chamber, is applied to said plunger thereby releasing said engagement means, allowing said relative movement of said inner sleeve with respect to said outer housing so that said cutter cuts through said stopper and said flange thereby allowing said bias of said spring to urge a sufficient movement of said stem having said needle mounted therein into said cavity in said inner sleeve thereby substantially preventing inadvertent exposure of said point of said needle.

2. The syringe of claim 1 wherein said sidewall of said inner sleeve further comprises a proximal portion having at least one slot therethrough and wherein said releasable engagement means further comprises a thumbpress fit within said inner sleeve having at least one flexible lug sized and shaped to protrude through said slot in said inner sleeve and substantially prevent said movement of said inner sleeve with respect to said outer housing, thereby allowing proximal and distal movement of said stopper within said barrel for drawing and expelling fluid from said chamber, said at least one flexible lug being disposed to engage said proximal end of said barrel when sufficient distal force, greater than the force required to expel fluid from said chamber, is applied to said plunger thereby deflecting said lug inwardly and allow distal movement of said inner sleeve with respect to said outer housing so that said cutter cuts through said stopper and said flange.

3. The syringe of claim 1 wherein said thumbpress further comprises two flexible lugs and said distal portion of said inner sleeve further comprises two cooperating slots in said sidewall.

4. The syringe of claim 3 wherein said engagement means further comprises an enlarged area of said distal portion of said inner sleeve disposed to provide a detent with said outer housing, said detent being overcome by said distal force greater than the force required to expel fluid from said chamber, and wherein said force required to overcome said detent is a load between about 8 to about 12 pounds, thereby allowing at least one lugs to engage said proximal end of said barrel.

5. The syringe of claim 4 wherein said distal force to deflect said at least one lug, greater than the force required to expel fluid from said chamber, is a load greater than about 15 pounds thereby to allow said axial movement of said inner sleeve with respect to said outer housing.

6. The syringe of claim 1 wherein said attachment for attaching said hub housing to said barrel is selectively detachable and further comprises conjugate cooperating threads on said distal end of said barrel and on said hub housing.

7. The syringe of claim 6 wherein said attachment for attaching said hub housing to said barrel further comprises internal female threads on said distal end of said barrel and conjugate cooperating external male threads on said hub housing.

8. The syringe of claim 7 wherein said distal end of said barrel further comprises an inwardly extending seal to engage said flange of said inner hub when said hub housing having said hub disposed therein is thereby to form a substantially fluid tight seal between said flange and said barrel.

9. The syringe of claim 1 wherein said distal end of said hub housing and said stem of said hub are substantially flush and wherein a distal portion of said passage has an enlarged tapered portion to facilitate mounting of proximal end of said needle in said passage.

10. The syringe of claim 1 being sealed in a package formed from materials substantially resistant to the passage of microorganisms and exposed to conditions that render microorganisms therein substantially non-viable.

11. The syringe of claim 1 wherein said inner sleeve further comprises said engagement means being integrally formed as a single article of manufacture.

12. The syringe of claim 11 wherein said engagement means integrally formed with said inner sleeve further comprises two cantilevers having extending a distance distally from said proximal end, each of said cantilevers including an outwardly extending lug disposed to engage said outer housing and substantially prevent axial movement of said inner sleeve with respect to said outer housing until said force, greater than the force required to expel fluid from said chamber, is applied to said plunger, and wherein said thumbpress comprises a plug inserted into said proximal end of said inner sleeve.

13. The syringe of claim 1 wherein said cutter is an elongate sleeve having a proximal socket for mounting said distal end of said inner sleeve and a distal sharpened edge to facilitate cutting through said stopper and said flange.

14. The syringe of claim 13 wherein said cutter is formed from a metallic material comprising stainless steel.

15. The syringe of claim 14 wherein said cutter is formed by a deep draw process and subjected to a secondary process selected from the group consisting of electrochemical treatment, grinding, honing, polishing and combinations thereof.

16. A hypodermic syringe with a selectively retractable needle comprising:

an elongate barrel having an open proximal end, an open distal end and a hollow bore therethrough;

an elongate plunger sized to fit slidably within said barrel, said plunger comprising a hollow outer housing having an open proximal end and an open distal end, a hollow inner sleeve having a sidewall defining a cavity therewithin, an open proximal end and an open distal end, said sidewall having two slots therethrough located adjacent said distal end, said inner sleeve disposed within and sized to fit slidably within said hollow outer housing, and a thumbpress having two flexible lugs disposed to extend outwardly through slots in said sidewall and releasably engage said outer housing thereby preventing relative axial movement between said outer housing and said inner sleeve, said lugs allowing said relative axial movement when released, said plunger further including a stopper mounted at said distal end of said outer housing for occluding said open distal end and sized to form a slidable seal with said hollow bore of said barrel to define a chamber for drawing and expelling fluid, and a open cutter mounted at said proximal end of said inner sleeve and disposed to cut through said stopper to expose said cavity in said inner sleeve when said inner sleeve is released for distal motion relative to said outer housing by sufficient distal axial force applied to said plunger;

a hub housing having an open proximal end having an inwardly projecting shoulder, a passageway therethrough having an inside surface, a distal end and an attachment for attaching said hub to said proximal end of said barrel;

a hub comprising a proximal flange, an axial stem with a distal end having a passage therethrough, said hub sized to fit within said hub housing with said stem extending distally and said flange defining a distal end of said chamber;

an elongate spring disposed about said stem and compressed to provide a bias between said flange and said inwardly projecting shoulder of hub housing;

an elongate needle having a sharp distal point, a proximal end and a fluid path therethrough, said needle being mounted in said passage in said hub with said distal point extending outwardly and said fluid path in communication with said chamber, said needle being retracted into said cavity in said plunger when sufficient distal force, greater than the force required to expel fluid from said chamber, is applied to said plunger thereby releasing said lugs from said outer housing allowing said relative movement of said inner sleeve with respect to said outer housing so that said cutter cuts through said stopper and said flange thereby allowing said bias of said spring to urge a sufficient movement of said stem having said needle mounted therein into said cavity in said inner sleeve thereby substantially preventing inadvertent exposure of said point of said needle.

* * * * *